(12) United States Patent
Kurosaki et al.

(10) Patent No.: US 12,318,562 B2
(45) Date of Patent: Jun. 3, 2025

(54) BALLOON FOLDING METHOD

(71) Applicant: TERUMO KABUSHIKI KAISHA, Tokyo (JP)

(72) Inventors: Yasuo Kurosaki, Kanagawa (JP); Hiroshi Goto, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 922 days.

(21) Appl. No.: 17/479,026

(22) Filed: Sep. 20, 2021

(65) Prior Publication Data

US 2022/0001153 A1   Jan. 6, 2022

Related U.S. Application Data

(63) Continuation of application No. PCT/JP2020/012225, filed on Mar. 19, 2020.

(30) Foreign Application Priority Data

Mar. 22, 2019   (JP) .................................. 2019-055361

(51) Int. Cl.
*B29C 53/08* (2006.01)
*A61M 25/10* (2013.01)
(Continued)

(52) U.S. Cl.
CPC .. *A61M 25/1038* (2013.01); *A61M 25/10181* (2013.11); *B29C 53/005* (2013.01);
(Continued)

(58) Field of Classification Search
CPC .............................. B29C 53/08; B29C 53/086
See application file for complete search history.

(56) References Cited

U.S. PATENT DOCUMENTS

| 2002/0163104 A1 | 11/2002 | Motsenbocker et al. |
| 2003/0163157 A1 | 8/2003 | McMorrow et al. |

(Continued)

FOREIGN PATENT DOCUMENTS

| CN | 102458566 A | 5/2012 |
| CN | 108025164 A | 5/2018 |

(Continued)

OTHER PUBLICATIONS

Office Action (The First Office Action) issued Feb. 2, 2023, by the State Intellectual Property Office of People's Republic of China in corresponding Chinese Patent Application No. 202080007103.4. (7 pages).

(Continued)

*Primary Examiner* — Atul P. Khare
(74) *Attorney, Agent, or Firm* — Buchanan Ingersoll & Rooney PC

(57) ABSTRACT

A folding method of an inflatable balloon disposed on an outer peripheral surface of an inner tube of a balloon catheter is disclosed. The method includes: disposing the balloon to an inner side of a plurality of first blade portions arranged so as to surround a reference position while maintaining a state where pressure is applied to an inside of the balloon; correcting a bend of the balloon by moving the plurality of first blade portions toward the reference position in the state where the pressure is applied to the inside of the balloon; pleating a plurality of wing portions protruding radially outward on the balloon by further moving the plurality of first blade portions toward the reference position to partially press the balloon while gradually discharging the fluid inside the balloon; and folding the balloon along the inner tube.

16 Claims, 6 Drawing Sheets

(51) Int. Cl.
  *B29C 53/00*  (2006.01)
  *B29C 53/06*  (2006.01)
(52) U.S. Cl.
  CPC .......... *B29C 53/063* (2013.01); *B29C 53/086* (2013.01); *A61M 2025/1031* (2013.01)

(56) References Cited

U.S. PATENT DOCUMENTS

| | | | |
|---|---|---|---|
| 2011/0130708 A1 | 6/2011 | Perry et al. | |
| 2018/0207410 A1 | 7/2018 | Kurosaki et al. | |
| 2019/0192833 A1 | 6/2019 | Kurosaki et al. | |
| 2022/0001147 A1* | 1/2022 | Goto | A61M 25/1038 |

FOREIGN PATENT DOCUMENTS

| | | | | |
|---|---|---|---|---|
| JP | 2004188492 A | * | 7/2004 | |
| JP | 2004525704 A | | 8/2004 | |
| JP | 2005518880 A | | 6/2005 | |
| JP | 2006271678 A | | 10/2006 | |
| JP | 2013056071 A | | 3/2013 | |
| JP | 2017060615 A | * | 3/2017 | |
| JP | 2017060616 A | * | 3/2017 | |
| JP | 2017060617 A | * | 3/2017 | |
| JP | 2017060619 A | * | 3/2017 | |
| JP | 2017169733 A | * | 9/2017 | |
| JP | 2017169734 A | * | 9/2017 | |
| JP | 2017169735 A | * | 9/2017 | |
| JP | 2017169736 A | * | 9/2017 | |
| JP | 2017169737 A | * | 9/2017 | |
| WO | 2018056389 A1 | | 3/2018 | |

OTHER PUBLICATIONS

Office Action (Notice of Reasons for Refusal) issued Sep. 19, 2023, by the Japan Patent Office in corresponding Japanese Patent Application No. 2021-509297 and an English translation of the Office Action. (9 pages).

Office Action (Notice of Reasons for Refusal) issued Jun. 5, 2023, by the Japan Patent Office in corresponding Japanese Patent Application No. 2021-509297 and an English translation of the Office Action. (9 pages).

International Search Report (PCT/ISA/210) with translation and Written Opinion (PCT/ISA/237) mailed on Jun. 2, 2020, by the Japanese Patent Office as the International Searching Authority for International Application No. PCT/JP2020/012225. (10 pages).

\* cited by examiner

BALLOON FOLDING METHOD

This application is a continuation of International Application No. PCT/JP2020/012225 filed on Mar. 19, 2020, which claims priority to Japanese Application No. 2019-055361 filed on Mar. 22, 2019, the entire content of both of which is incorporated herein by reference.

FIELD OF THE DISCLOSURE

The present disclosure relates to a method of folding a balloon of a balloon catheter.

BACKGROUND DISCUSSION

In recent years, balloon catheters are used for improving a lesion area generated in a living body lumen. The balloon catheter is normally provided with an elongated shaft, and a balloon provided at a distal side of the shaft and is inflatable in a radial direction. The balloon can expand a lesion area by being pressed into a target location inside the body through a thin living body lumen, and thereafter being inflated.

In a manufacturing process of a balloon catheter, generally, a balloon is folded so as to be wound around a shaft of the catheter in order to deflate the balloon to a small diameter. For example, in Japanese Patent Application Publication No. 2004-525704 A, wing portions protruding in a radial direction of a balloon are pleated on the balloon, the wing portions are folded so as to be wound around a shaft of a catheter. At the process of pleating the wing portions, the balloon is inserted into the center of a plurality of members arranged so as to surround a predetermined range, and those members are moved toward a radial inner side of the balloon, thereby pleating the wing portions on the balloon.

For example, a balloon that is relatively long in the axis direction, such as a balloon for a lower limb, is rather easily curved. If the balloon is curved, when the wing portions are pleated, the center of the members arranged so as to pleat the wings and the center of the balloon are rather easily shifted. Accordingly, there is a possibility that the protrusion lengths of the wing portions to be pleated on the balloon may be uneven.

SUMMARY

A folding method of a balloon capable of uniformly pleating a plurality of wing portions protruding radially outward on the balloon and folding the plurality of wing portions is disclosed.

A folding method of an inflatable balloon disposed on an outer peripheral surface of a shaft of a balloon catheter is disclosed, the folding method including: disposing the balloon to an inner side of a plurality of blade portions arranged so as to surround a reference position while maintaining a state where pressure is being applied to an inside of the balloon; correcting a bend (a curve) of the balloon by moving the blade portions toward the reference position in the state where the pressure is being applied to the inside of the balloon; pleating a plurality of wing portions protruding radially outward on the balloon by further moving the blade portions toward the reference position while gradually discharging a fluid in the inside of the balloon to partially press the balloon; and folding the plurality of wing portions along the shaft.

In the folding method of a balloon configured as the above, before the plurality of wing portions are pleated on the balloon, the balloon is moved toward the reference position by the blade portions. In this case, the balloon in a pressure-applied state is difficult to deform even pressed by the blade portions. Therefore, in the folding method of a balloon, it is possible to effectively correct the bend of the balloon by moving the balloon toward the reference position by the blade portions. Accordingly, in this folding method of a balloon, it is possible to uniformly pleat and fold the plurality of wing portions.

In the folding method of a balloon, the plurality of wing portions of the balloon may be heated upon pleating the wing portions or subsequent steps. Accordingly, it is possible to properly maintain the shape of the uniformly pleated plurality of wing portions of the balloon.

In the folding method of a balloon, upon correcting the bend of the balloon, the blade portions may be vibrated. Accordingly, it is possible to guide the balloon to a suitable position by the vibration, and to uniformly pleat the plurality of wing portions of the balloon.

The folding method of a balloon may include: regulating an inflow of the fluid to the inside of the balloon after the step of pleating the plurality of wing portions; and coating a surface of the balloon with a drug. Accordingly, in a state where the shape of the balloon is held after the plurality of wing portions have been pleated, the surface of the balloon can be appropriately coated with the drug. Moreover, because the outer surface of the balloon is coated with the drug after the plurality of wing portions have been pleated, the outer surface of the balloon is not coated with the drug when the plurality of wing portions are pleated. Therefore, when the plurality of wing portions are pleated on the balloon, the separation of the drug from the balloon can be suppressed.

In folding method of a balloon, upon correcting the bend of the balloon and the pleating of the plurality of the wing portions, a flexible film may be interposed between the blade portions and the balloon, and upon folding the plurality of wing portions, a flexible film may be interposed between a plurality of second blade portions arranged so as to surround the balloon in order to fold the plurality of wing portions and the balloon. Accordingly, when the bend of the balloon is corrected, when the plurality of wing portions are pleated on the balloon, and when the plurality of wing portions are folded, it is possible to protect the surface of the balloon by the films, and suppress the separation of the drug from the balloon.

In accordance with an aspect, a folding method of an inflatable balloon disposed on an outer peripheral surface of an inner tube of a balloon catheter, the method comprising: disposing the balloon to an inner side of a plurality of first blade portions of a balloon folding device; injecting an inflation fluid into the balloon to obtain a pressure-applied state of the balloon; moving the first blade portions toward the balloon in the pressure-applied state; moving the plurality of first blade portions into contact with the balloon in the pressure-applied state; and pleating a plurality of wing portions protruding radially outward on the balloon with the plurality of first blade portions while gradually discharging the inflation fluid from the inside of the balloon.

In accordance with another aspect, a folding method of a balloon disposed on an outer peripheral surface of a shaft of a balloon catheter, the method comprising: disposing the balloon to an inner side of a plurality of blade portions of a balloon folding device while maintaining a state where pressure is being applied to an inside of the balloon; correcting a bend of the balloon by moving the plurality of first blade portions toward the balloon while the pressure is being applied to the inside of the balloon; and pleating a plurality of wing portions protruding radially outward on the balloon by further moving the plurality of first blade portions toward the balloon while gradually discharging a fluid from the inside of the balloon

DETAILED DESCRIPTION

Set forth below with reference to the accompanying drawings is a detailed description of embodiments of a method of folding a balloon of a balloon catheter. Note that since embodiments described below are preferred specific examples of the present disclosure, although various technically preferable limitations are given, the scope of the present disclosure is not limited to the embodiments unless otherwise specified in the following descriptions. Note that, the dimensions on the drawings may be exaggerated for convenience of description, and may be different from the actual dimensions in some cases. Moreover, in the present specification and the drawings, the same reference signs are given to the components having substantially the same functions, and overlapped descriptions of the components are thus omitted. In the present specification, a side of a balloon catheter to be inserted into a blood vessel is referred to as a "distal side", and a hand-side at which the balloon catheter is operated is referred to as a "proximal side".

Figure 1:
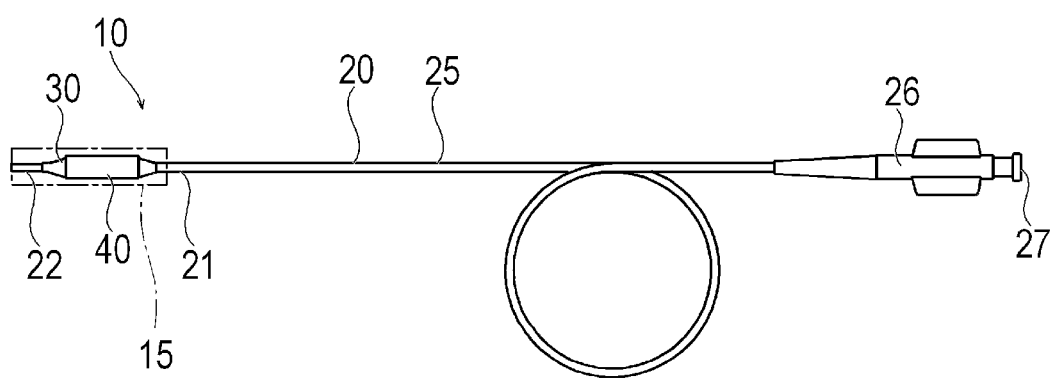
FIG. 1 is a front view illustrating a balloon catheter.
Figure 2:
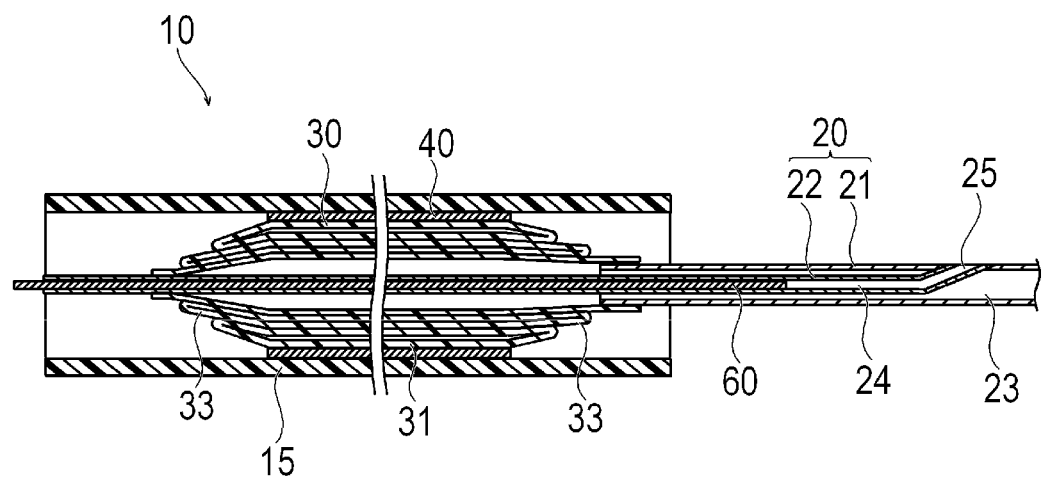
FIG. 2 is a cross-sectional view of a distal portion of the balloon catheter.

A folding method of a balloon according to the embodiment of the present disclosure is, as illustrated in FIGS. 1 and 2, a folding method of a balloon 30 of a balloon catheter 10 with respect to a shaft to which the balloon 30 is fixed. The balloon catheter 10 is a device that is inserted into a lumen of a living body such as a blood vessel and is pressed to a stenosed lesion area, and expands the lesion area by the inflatable balloon 30.

Firstly, a structure of the balloon catheter 10 will be described. The balloon catheter 10 includes an elongated catheter main body 20, the balloon 30 that is provided to a distal portion of the catheter main body 20, a drug-coated layer 40 including a drug that is provided at an outer surface of the balloon 30, and a hub 26 secured to a proximal portion of the catheter main body 20. The balloon 30 coated with the drug-coated layer 40 is covered and protected by a protective tube 15 before use.

The catheter main body 20 is provided with an outer tube 21 that is a tubular body having an open distal side end portion and an open proximal side end portion, and an inner tube 22 (shaft) that is a tubular body to be disposed in an inside of the outer tube 21. The inner tube 22 is contained in the hollow inside of the outer tube 21, and the catheter main body 20 has a double tubular structure in the distal portion. The inner tube 22 includes a hollow inside, which is a guide wire lumen 24 through which a guide wire can be inserted. Moreover, an inflation lumen 23 in which an inflation fluid of the balloon 30 is communicated is formed in the hollow inside of the outer tube 21 and on an outer side of the inner tube 22. The inner tube 22 is opened to the outside in an opening portion 25 that penetrates a wall surface of the outer tube 21 in a side direction. The inner tube 22 protrudes further to the distal side than a distal end of the outer tube 21 (i.e., a distal end of the inner tube 22 is distal to the distal end of the outer tube 21).

The balloon 30 has a proximal side end portion that is fixed to a distal portion of the outer tube 21, and a distal side end portion that is fixed to a distal portion of the inner tube 22. Accordingly, the inside of the balloon 30 communicates with the inflation lumen 23. The inflation fluid is injected to the balloon 30 through the inflation lumen 23, whereby the balloon 30 can be caused to inflate. The inflation fluid may be gas or a liquid, and for example, the gas such as a helium gas, a $CO_2$ gas, or an $O_2$ gas, and the liquid can be, for example, saline (i.e., a saline solution) or a contrast agent.

In a center portion in a longitudinal direction of the balloon 30, a cylindrical straight portion 31 having an equal outer diameter when the balloon is caused to inflate is formed, and tapered portions 33 having an outer diameter that gradually changes are formed on both sides in a longitudinal direction of the straight portion 31. Further, an entire outer surface of the straight portion 31 is coated with the drug-coated layer 40 including the drug. Note that, a range in which the drug-coated layer 40 is formed in the balloon 30 is not limited only to the straight portion 31, but may include at least a part of the tapered portions 33, in addition to the straight portion 31, or may include only a part of the straight portion 31.

In the hub 26, a proximal opening portion 27 serving as a port that communicates with the inflation lumen 23 of the outer tube 21 and causes the inflation fluid to flow in and out of the inflation lumen 23 is formed.

The length in the longitudinal direction of the balloon 30 is not specially limited, and can be, for example, 5 mm to 500 mm, preferably 10 mm to 300 mm, and more preferably 20 mm to 200 mm. The folding method of a balloon according to the present embodiment may be effective for, for example, the balloon 30 that is relatively long in the longitudinal direction and rather easily bends (curves), such as the balloon 30 for a lower limb. The length in the longitudinal direction of the balloon 30 that is relatively long in the longitudinal direction can be, for example, 40 mm to 300 mm, preferably 80 mm to 300 mm, and more preferably 100 to 300 mm.

The outer diameter of the balloon 30 when inflating is not specially limited, and can be, for example, 1 mm to 10 mm, and preferably 2 mm to 8 mm.

The material of the balloon 30 preferably has flexibility to some extent, and hardness to some extent such that the balloon 30 is caused to inflate when reaching a blood vessel, a tissue, or the like, and the drug can be released from the drug-coated layer 40 on the surface of the balloon 30. Specifically, the material of the balloon 30 includes resin and metal, and at least the outer surface of the balloon 30 on which the drug-coated layer 40 is provided preferably includes resin. The material for at least the outer surface of the balloon 30 can include, for example, a polyolefin such as polyethylene, polypropylene, polybutene, an ethylene-propylene copolymer, an ethylene-vinyl acetate copolymer, an ionomer, or a mixture of two or more of the polyolefins, the ethylene-vinyl acetate copolymer, and/or the ionomer, a soft polyvinyl chloride resin, a thermoplastic resin such as polyamide, a polyamide elastomer, a nylon elastomer, a polyester, a polyester elastomer, polyurethane, and fluorine resin, silicone rubber, latex rubber, and the like can be used. Among the materials for at least the outer surface of the balloon main body 31, polyamides can be preferred.

The drug-coated layer 40 contains a drug. The drug-coated layer 40 may also contain an additive agent (excipient). The drug may be a crystalline type, an amorphous type, or a mixture of the crystalline type and the amorphous type. In a case where the drug is a crystalline type, for example, homogeneous (white) crystals can be formed on the entire circumference of the balloon 30 (substantially contain no amorphousness).

The drug may be a water-soluble drug, but is preferably a water-insoluble drug. The water-insoluble drug indicates a drug that is insoluble or poorly-soluble in water, and specifically, the solubility in water is less than 1 mg/mL at pH5 to 8. The solubility, for example, may be less than 0.1 mg/mL. The water-insoluble drug includes a fat-soluble drug.

Examples of some preferred water-insoluble drugs include immunosuppressive agents, such as cyclosporins including cyclosporine, immunoactive agents such as rapamycin, anticancer agents such as paclitaxel, antiviral agents or antimicrobial agents, antineoplastic agents, analgesic agents and anti-inflammatory agents, antibiotics, antiepileptics, anxiolytics, anticonvulsant agents, antagonists, neuron blocking agents, anticholinergics and cholinergic agents, antimuscarinic and muscarinic agents, antiadrenergic agents, antiadrenergic agents, antiarrhythmic agents, antihypertensive agents, hormonal agents, and nutritional agents.

In accordance with an exemplary embodiment, the water-insoluble drug is preferably at least one selected from the group consisting of rapamycin, paclitaxel, docetaxel, and everolimus. In the present specification, rapamycin, paclitaxel, docetaxel, and everolimus each include analogs and/or derivatives of rapamycin, paclitaxel, docetaxel, and everolimus as long as they have similar medicinal properties. For example, paclitaxel and docetaxel are in an analog relationship. Rapamycin and everolimus are in a derivative relationship. Among these, paclitaxel is further preferable.

The additive agent is not specially limited, and can include, for example, a water-soluble low molecular weight compound. The molecular weight of the water-soluble low molecular weight compound can be, for example, 50 to 2000, preferably 50 to 1000, more preferably 50 to 500, and further more preferably 50 to 200. The water-soluble low molecular weight compound can be, for example, relative to 100 parts by mass of the water-insoluble drug, preferably 10 to 5000 parts by mass, more preferably 50 to 3000 parts by mass, and further more preferably 100 to 1000 parts by mass. The material for the water-soluble low molecular weight compound can be, for example, serine ethyl ester, saccharide such as glucose, sugar alcohol such as sorbitol, a citric acid ester, polysorbate, polyethylene glycol, urea, a water-soluble polymer, a contrast agent, an amino acid ester, a glycerol ester of a short chain monocarboxylic acid, a salt and a surface-active agent allowable as a pharmaceutical preparation, a mixture of two or more of the above-mentioned materials for the water-soluble low molecular weight compound.

A method of forming the drug-coated layer 40 on the balloon 30 is not specially limited. For example, the balloon 30 may be caused to move in the longitudinal direction while being caused to rotate about an axial center of the balloon, and a coating liquid including, for example, a drug, an additive agent, and a solvent may be applied to the surface of the balloon so as to draw a spiral on an outer surface of the balloon 30. Evaporation of a solvent in the coating liquid applied on the surface of the balloon forms the drug-coated layer 40. Alternatively, the drug-coated layer 40 may be formed by dipping the balloon 30 into the coating liquid, or spraying the coating liquid on the outer surface of the balloon 30.

The protective tube 15 is a member that covers and protects the balloon 30, and suppresses separation of the drug from the balloon 30. The protective tube 15 can include a flexible material, and for example, a polyolefin such as polyethylene, polypropylene, polybutene, an ethylene-propylene copolymer, an ethylene-vinyl acetate copolymer, an ionomer, or a mixture of two or more of the flexible materials of the protective tube 15, soft polyvinyl chloride resin, thermoplastic resin such as polyamide, a polyamide elastomer, polyester, a polyester elastomer, polyurethane, and fluorine resin, silicone rubber, latex rubber, and the like can be used.

Next, a balloon folding device 100 will be described. The balloon folding device 100 is a device that can fold the balloon 30 so as to be wound around the inner tube 22.

Figure 3:
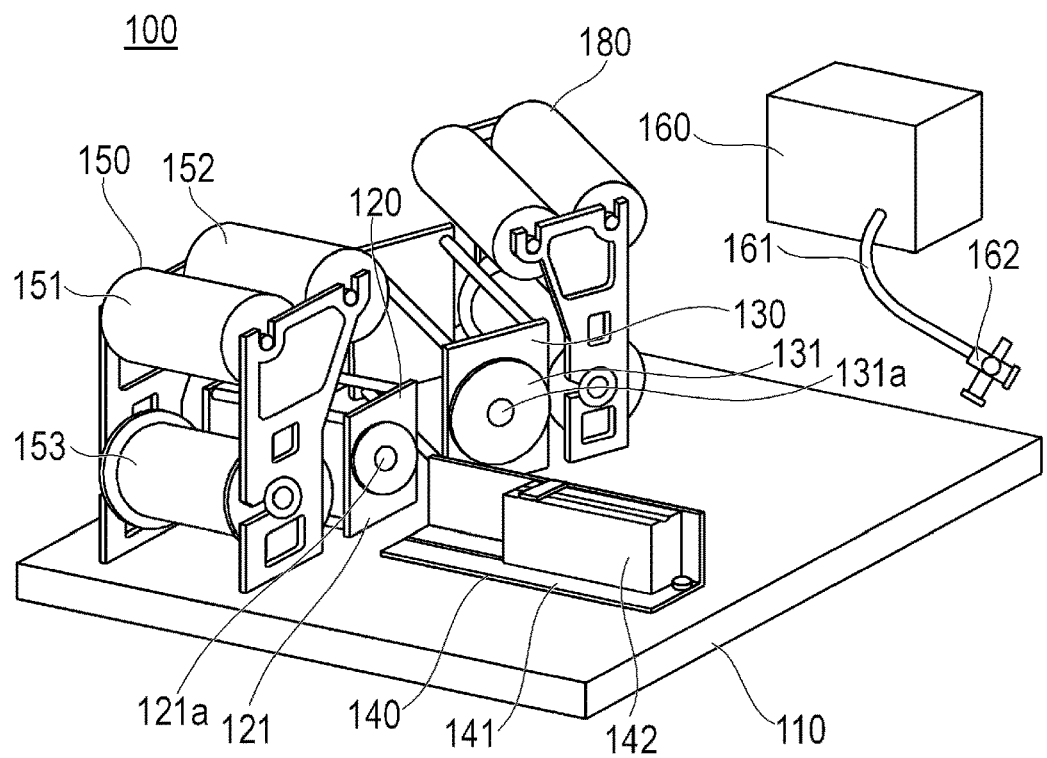
FIG. 3 is a perspective view illustrating a balloon folding device.

The balloon folding device 100 includes, as illustrated in FIG. 3, a base 110, a pleating section 120, a folding section 130, a support mount 140, and a pressure applying/reducing device 160. The pleating section 120, the folding section 130, and the support mount 140 are disposed on the base 110 formed in a base shape (i.e., relatively flat surface).

Figure 10:
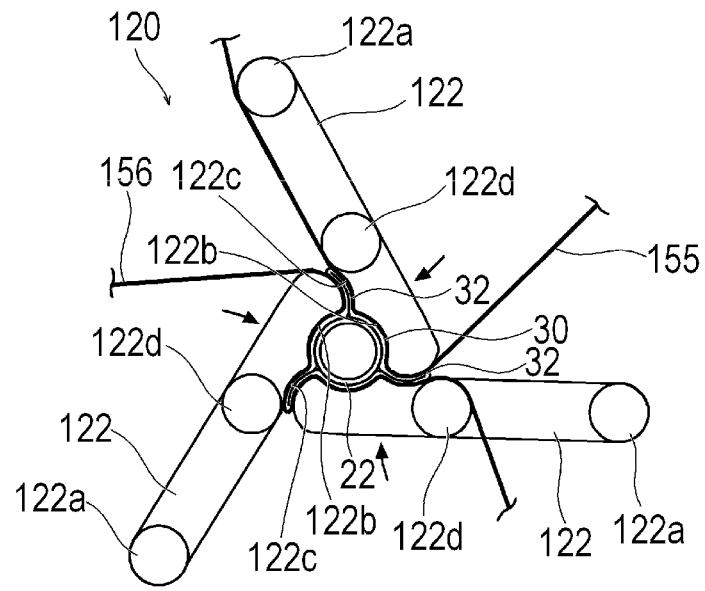
FIG. 10 is a cross-sectional view illustrating a state where wing portions are pleated on the balloon by the pleating section.
Figure 11:
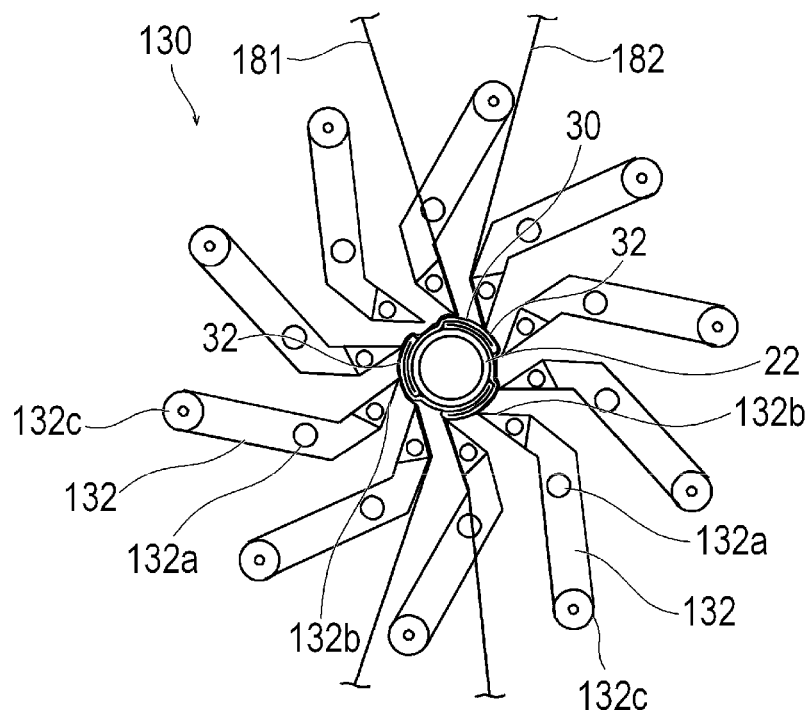
FIG. 11 is a cross-sectional view illustrating a state where the wing portions are folded by the folding section.

The pleating section 120 can pleat the plurality of wing portions 32 of the balloon 30 that protrude in the radial direction on the balloon 30, as illustrated in FIG. 10. The plurality of wing portions 32 are pleats, and long and narrow folds that are formed in a relatively thin material of the balloon 30. The plurality of wing portions 32 to be pleated on the balloon 30 are formed of folds extending in a substantial longitudinal direction of the balloon 30. When viewed in a cross section perpendicular to an axial center of the balloon 30, the plurality of wing portions 32 are pleated so as to protrude radially outward of the balloon 30. The length in the longitudinal direction of the plurality of wing portions 32 does not exceed the length of the balloon 30. The length in a direction in which the plurality of wing portions 32 protrude radially outward from the catheter main body 20 can be, for example, approximately 1 mm to 8 mm. The number of the plurality of wing portions 32 is not specially limited, and can be about 2 wing sheets to 7 wing sheets, for example. The folding section 130 can lay and fold the plurality of wing portions 32 pleated on the balloon 30, in a circumferential direction, as illustrated in FIG. 11. The support mount 140 can hold the balloon catheter 10 while the plurality of wing portions 32 are pleated on the balloon 30 and folded, as illustrated in FIG. 3. The pressure applying/reducing device 160 can supply a fluid to the inside of the balloon 30 to apply pressure, and can aspirate the fluid from the inside of the balloon 30 to reduce pressure.

A film supply section 150 that supplies a first film 155 and a second film 156 to the pleating section 120 is disposed adjacent to the pleating section 120, on the base 110. Moreover, a film supply section 180 that supplies a first film 181 and a second film 182 to the folding section 130 is disposed on the base 110 adjacent to the folding section 130.

The pleating section 120 can include a front surface plate 121 perpendicular to the base 110, and the front surface plate 121 can include an insertion hole 121a through which a distal portion of the balloon catheter 10 can be inserted. Moreover, the folding section 130 can include a front surface plate 131 perpendicular to the base 110, the front surface plate 131 can include an insertion hole 131a through which the distal portion of the balloon catheter 10 can be inserted. The front surface plate 131 of the folding section 130 faces toward a direction different from a direction toward which the front surface plate 121 of the pleating section 120 faces.

The support mount 140 is rotatable so as to face toward both of a position facing the pleating section 120 and a position facing the folding section 130. The support mount 140 can include a base portion 141 that can be rotatably mounted on the base 110, and a holding stand 142 that is horizontally movable on the base portion 141. The holding stand 142 can hold the balloon catheter 10 on an upper surface of the holding stand 142. The holding stand 142 moves by sliding on an upper surface of the base portion 141, and can move forward or backward toward the pleating section 120 or the folding section 130. The holding stand 142 holding the balloon catheter 10 moves forward or backward toward the pleating section 120, whereby the balloon 30 is inserted into or pulled out from the insertion hole 121a of the pleating section 120. Moreover, the holding stand 142 holding the balloon catheter 10 moves forward or backward toward the folding section 130, whereby the balloon 30 is inserted into or pulled out from the insertion hole 131a of the folding section 130.

The pressure applying/reducing device 160 can be, for example, a pump. The pressure applying/reducing device 160 may be a syringe, an indeflator, or the like. The pressure applying/reducing device 160 can include a pressure applying/reducing tube 161 that can be coupled to the proximal opening portion 27 of the balloon catheter 10. The pressure applying/reducing tube 161 supplies a fluid to the proximal opening portion 27, and aspirates the fluid from the proximal opening portion 27. The pressure applying/reducing tube 161 may be provided with a stopcock 162 that can be manually operated to open and close. The stopcock 162 can be, for example, a three-way stopcock.

Figure 4:
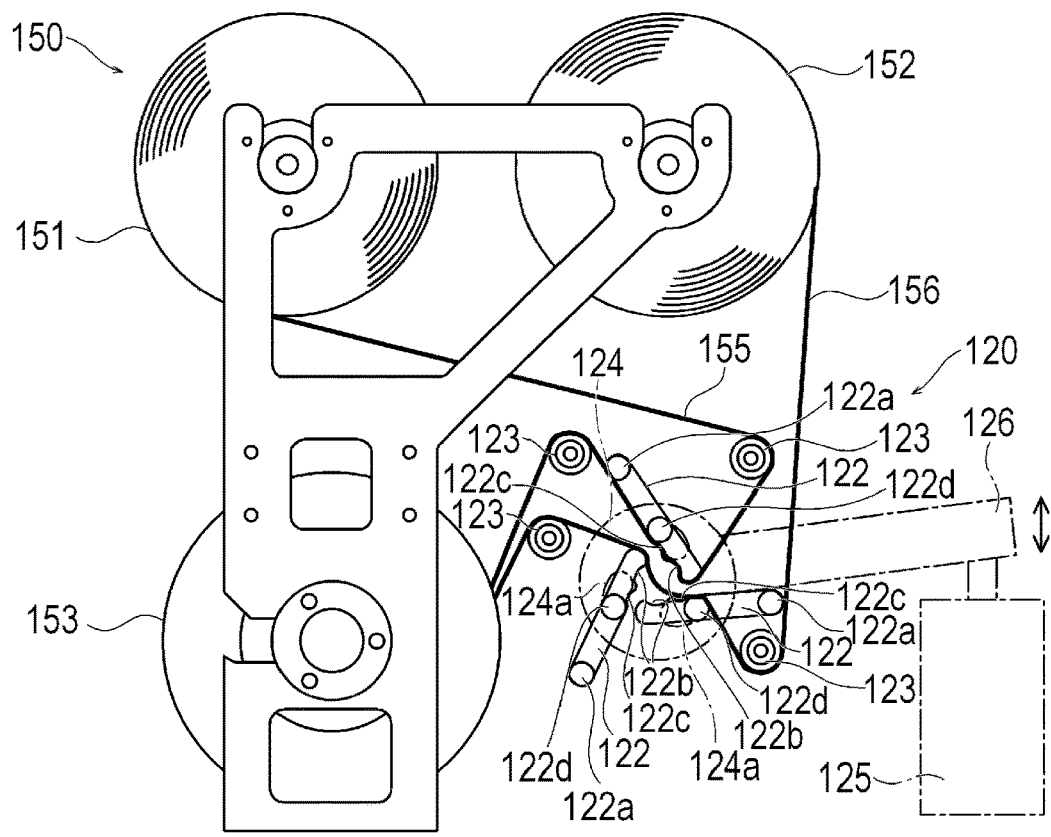
FIG. 4 is a front view illustrating a pleating section.
Figure 5:
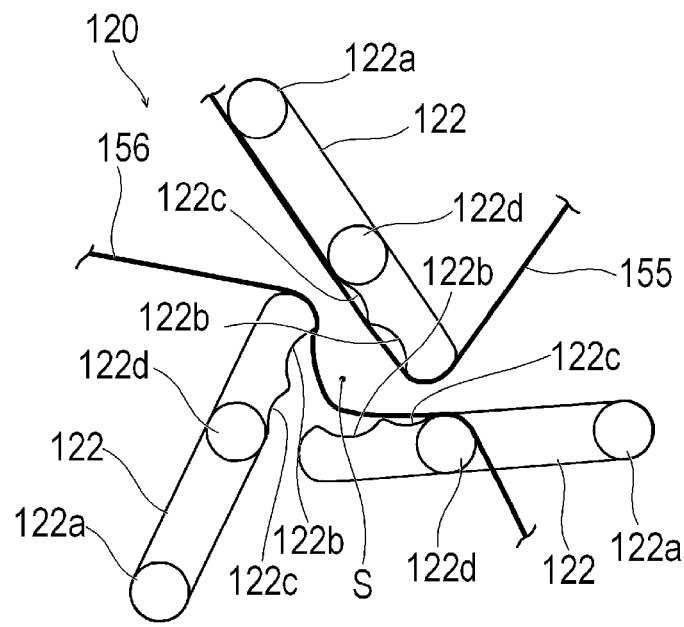
FIG. 5 is a front view illustrating first blade portions in the pleating section.

Next, the structure of the pleating section 120 will be described. The pleating section 120 includes a plurality of first blade portions 122 in an inside of the pleating section 120, as illustrated in FIGS. 4 and 5. The number of the first blade portions 122 is identical with the number of the plurality of wing portions 32 to be pleated on the balloon 30. Herein, a case where the three first blade portions 122 are provided will be described. Each of the first blade portions 122 is a plate-shaped member having a cross-sectional shape to be pleated in the same shape at each position along the longitudinal direction of the balloon catheter 10 to be inserted. The first blade portions 122 are disposed so as to each form an angle of 120 degrees relative to a linear reference position S that is positioned at the center of a center region in which the balloon 30 is inserted, and surround the center region. In other words, the respective first blade portions 122 are disposed at an equal angle in the circumferential direction. The first blade portion 122 includes a rotational-movement center portion 122a in the vicinity of an outer circumference end portion, and can move rotationally about the rotational-movement center portion 122a. Moreover, the first blade portion 122 includes a motion pin 122d extending in the longitudinal direction on an inner circumference side from the rotational-movement center portion 122a. The motion pin 122d is fitted into a fitting groove 124a that is formed in a rotation member 124 rotatable in the pleating section 120. The rotation member 124 is coupled to a beam portion 126 extending in a substantially horizontal direction. The rotation member 124 is rotatable by receiving a rotation force from the beam portion 126 that inclines by receiving a force from a drive source 125 such as a hydraulic cylinder or a motor. When the rotation member 124 rotates, the motion pin 122d that is fitted into the fitting groove 124a moves in the circumferential direction to move rotationally each of the first blade portions 122 about the rotational-movement center portion 122a. The three first blade portions 122 move rotationally to allow the center region surrounded by the first blade portions 122 to be narrowed. The number of the first blade portions 122 is not specially limited as long as the number of the first blade portions 122 is two or more.

The first blade portion 122 includes a first shape pleating portion 122b and a second shape pleating portion 122c, which are substantially arcuate, in an inner circumference end portion on the opposite side of the rotational-movement center portion 122a. The first shape pleating portions 122b contact the surface of the balloon 30 to be inserted into the pleating section 120 with the rotational-movement of the first blade portions 122 to allow the wing portions 32 protruding in the radial direction to be pleated on the balloon 30. The second shape pleating portion 122c can curve the wing portions 32 in a predetermined direction by contacting the wing portions to be pleated on the balloon 30 with the rotational-movement of the first blade portion 122. Moreover, the pleating section 120 can include a heater for heating the first blade portions 122. The pleating section 120 does not need to include the heater for heating the first blade portions 122. The length of the first blade portion 122 along the longitudinal direction of the balloon catheter 10 is longer than the length of the balloon 30. Moreover, the length of the first shape pleating portion 122b and the second shape pleating portion 122c of the first blade portion 122 may extend over or does not need to extend over a total length of the first blade portion 122.

The first film 155 and the second film 156, which can be made of resin, are supplied to the first blade portions 122 from the film supply section 150. A plurality of rotation axis portions 123 are provided in the pleating section 120 in order to guide the respective films. The first film 155 spreads on the surface of the first blade portion 122 disposed in an upper part, from a first film holding portion 151 via the rotation axis portion 123. Moreover, the first film 155 reaches from the first blade portion 122 through the rotation axis portion 123, to a film take-up portion 153 that is rotationally driven by a drive source, for example, such as a motor. The second film 156 spreads on the two first blade portions 122 disposed in a lower part from a second film holding portion 152 via the rotation axis portion 123. Moreover, the second film 156 reaches the film take-up portion 153 through the rotation axis portion 123. With these configurations, a center position of the pleating section 120 through which the balloon 30 is inserted is in a state of being surrounded by the first film 155 and the second film 156.

The first film 155 and the second film 156 protect the balloon 30 so as not to directly contact the surfaces of the first blade portions 122 when the balloon 30 is inserted into the pleating section 120, and the first blade portions 122 rotate to pleat the wing portions 32 on the balloon 30. After the wing portions 32 of the balloon 30 have been pleated, the first film 155 and the second film 156 are wound up on the film take-up portion 153 by a predetermined length. In other words, portions in the first film 155 and the second film 156 having contacted the balloon 30 once do not come into contact with the balloon 30 again, but new portions of the first film 155 and the second film 156 are supplied to the center position of the pleating section 120 every time the balloon 30 is inserted.

As illustrated in FIG. 5, in a state before the insertion of the balloon 30, the first shape pleating portions 122*b* and the second shape pleating portions 122*c* of the three first blade portions 122 are in a state of being separated from one another. The region that is surrounded by the plurality of the first blade portions 122 is surrounded by the first shape pleating portions 122*b* having the substantially arcuate shape, and the inflated balloon 30 can be inserted through the region that is surrounded by the first shape pleating portions 122*b*.

Figure 6:
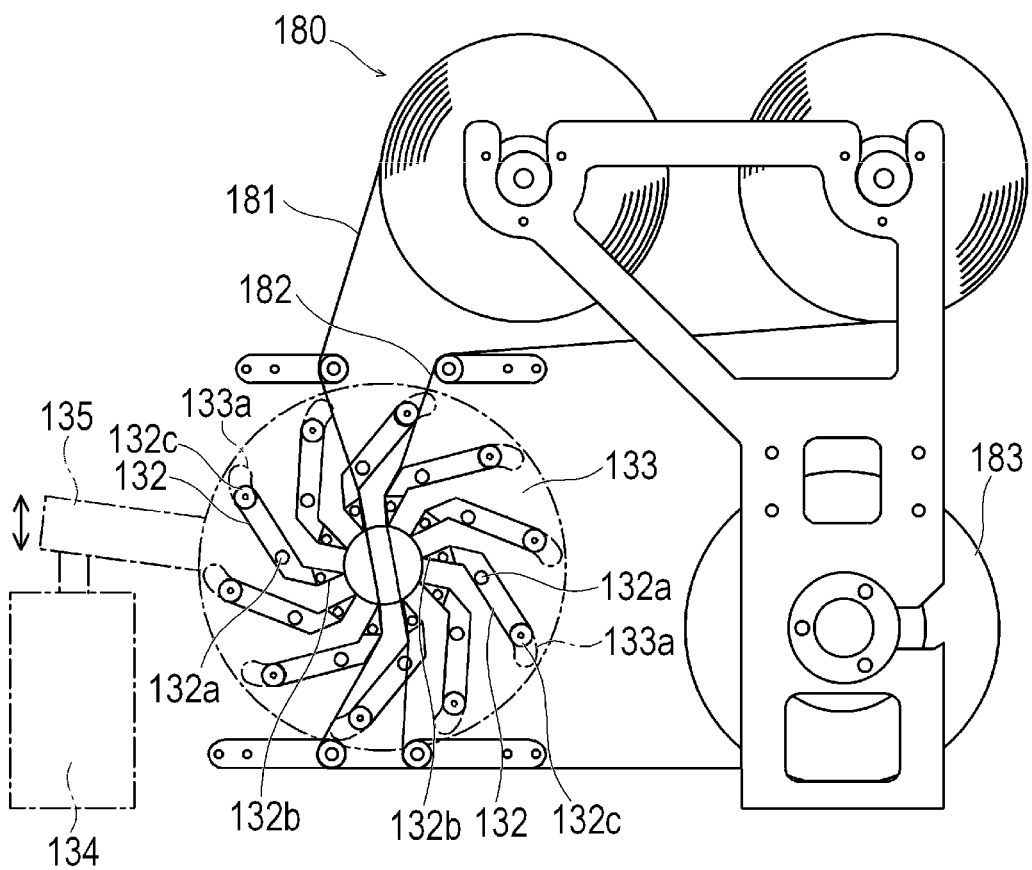
FIG. 6 is a front view illustrating a folding section.
Figure 7:
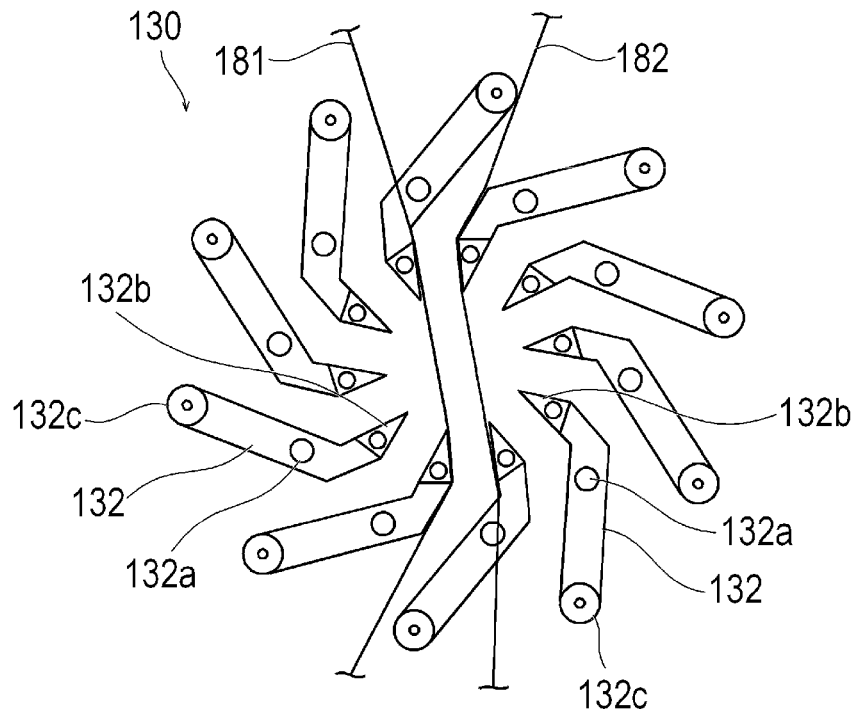
FIG. 7 is a front view illustrating second blade portions in the folding section.

Next, the structure of the folding section 130 will be described. The folding section 130 includes ten second blade portions 132 in an inside of the folding section 130, as illustrated in FIGS. 6 and 7. Each of the second blade portion 132 is a plate-shaped member having a cross-sectional shape to be pleated in the same shape at each position along the longitudinal direction of the balloon catheter 10 to be inserted. The second blade portions 132 are disposed so as to form each angle of 36 degrees relative to the center position at which the balloon is inserted. The respective second blade portions 132, for example, are disposed at an equal angle in the circumferential direction. The second blade portion 132 includes a rotational-movement center portion 132*a* in the vicinity of an approximately center of the second blade portion 132, and can move rotationally about the rotational-movement center portion 132*a*. Moreover, each second blade portion 132 includes a motion pin 132*c* extending in the axis direction in the vicinity of a generally outer circumference end portion of the second blade portion 132. The motion pin 132*c* is fitted into a fitting groove 133*a* that is formed in a rotation member 133 rotatable in the folding section 130. The rotation member 133 is coupled to a beam 135 extending in the substantially horizontal direction. The rotation member 133 is rotatable by receiving a rotation force from the beam 135 that inclines by receiving a force from a drive source 134 such as a hydraulic cylinder or a motor. When the rotation member 133 rotates, the motion pin 132*c* that is fitted into the fitting groove 133*a* moves in the circumferential direction to move rotationally each of the second blade portions 132 about the rotational-movement center portion 132*a*. The ten second blade portions 132 move rotationally to allow a space region in the center portion surrounded by the second blade portions 132 to be narrowed. The number of the second blade portions 132 is, for example, not limited to ten.

The second blade portion 132 is bent at a distal end side, and a distal end portion 132*b* has a pointed (bladed) shape. The distal end portions 132*b*, which come into contact with the surface of the balloon 30 to be inserted into the folding section 130 with the rotational-movement of the second blade portions 132, can fold the plurality of wing portions 32 pleated on the balloon 30 so as to be laid in the circumferential direction. Moreover, the folding section 130 can include a heater for heating the second blade portions 132. The folding section 130 does not need to include the heater for heating the second blade portions 132.

The first film 181 and the second film 182, which can be made of resin, are supplied to the second blade portions 132 from the film supply section 180. The supply structure of each film is similar to the case of the pleating section 120. The first film 181 and the second film 182 are disposed to face each other so as to sandwich the center space region surrounded by the second blade portions 132. The first film 181 and the second film 182 can prevent the balloon 30 inserted into the folding section 130 from directly contacting the surfaces of the second blade portions 132. The first film 181 and the second film 182 reach through the second blade portions 132 to a film take-up portion 183 that is rotationally driven by a drive source, for example, such as a motor.

As illustrated in FIG. 7, in a state before the insertion of the balloon 30, the distal end portions 132*b* of the respective second blade portions 132 are each in a separated state in the circumferential direction. The balloon 30 with the plurality of wing portions 32 pleated on the balloon 32 can be inserted between the first film 181 and the second film 182, which is a center region surrounded by the second blade portions 132.

Next, a method of folding the balloon 30 using the balloon folding device 100 will be described.

Firstly, as illustrated in FIG. 3, in order to pleat the plurality of wing portions 32 on the balloon 30, the catheter main body 20 is mounted on the holding stand 142 of the support mount 140. A core 60 is inserted into the guide wire lumen 24. A distal end of the core 60 is positioned distal to a distal end of the balloon 30. A proximal end of the core 60 may be positioned in the inside of the balloon 30, may be positioned distal to the opening portion 25 of the guide wire lumen 24 at the proximal side, or may be positioned proximal to the opening portion 25 of the guide wire lumen 24 at the proximal side. When the distal end of the core 60 is positioned distal to the distal end of the balloon 30, the length of the core 60 may be shorter than the length of the first blade portion 122 and the length of the second blade portion 132. The core 60 may have a length in the longitudinal direction overlapping with the whole of the first blade portions 122 and the whole of the second blade portions 132. Alternatively, the first blade portions 122 and the second blade portions 132 do not need to overlap with the opening portion 25 of the guide wire lumen 24 at the proximal side, in the longitudinal direction. Note that, the core 60 does not need to be inserted. The pressure applying/reducing tube 161 of the pressure applying/reducing device 160 is coupled to the proximal opening portion 27 of the balloon catheter 10. Further, when the pressure applying/reducing device 160 supplies a fluid, the fluid flows in the inside of the balloon 30 through the proximal opening portion 27 and the inflation lumen 23. Accordingly, the balloon 30 inflates to be in a pressure-applied state. The inflation pressure of the balloon 30 in the pressure-applied state can be, for example, 25% to 100%, preferably 50% to 100%, of the recommended inflation pressure. The recommended inflation pressure, can vary depending on the balloon 30. The pressure applying/reducing device 160 maintains the pressure-applied state after the balloon 30 has become the pressure-applied state. In order to maintain the pressure-applied state of the balloon 30, the pressure applying/reducing device 160 may successively apply pressure, or the stopcock 162 may be closed.

Figure 8:
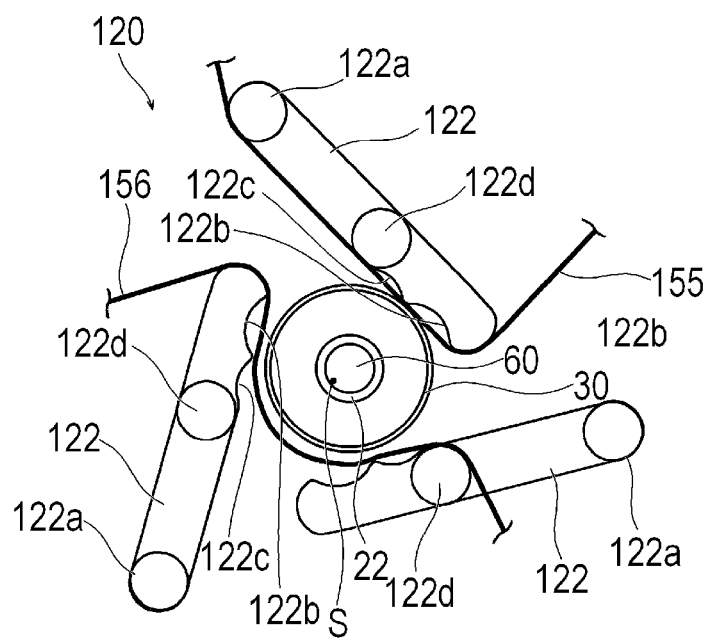
FIG. 8 is a cross-sectional view illustrating a state where a bent balloon is inserted into the pleating section.

Next, the holding stand 142 is moved by sliding on the base portion 141 to insert the balloon catheter 10 from the insertion hole 121*a* into the pleating section 120. The first blade portions 122 of the pleating section 120 is preferably heated, but do not need to be heated. In a case where the balloon 30 is relatively long in the longitudinal direction, the balloon 30 can rather easily bend. Therefore, as illustrated in FIG. 8, the balloon 30 is disposed in the center region that is surrounded by the plurality of first blade portions 122 with an axial center of the balloon 30 being shifted from the reference position S.

Figure 9:
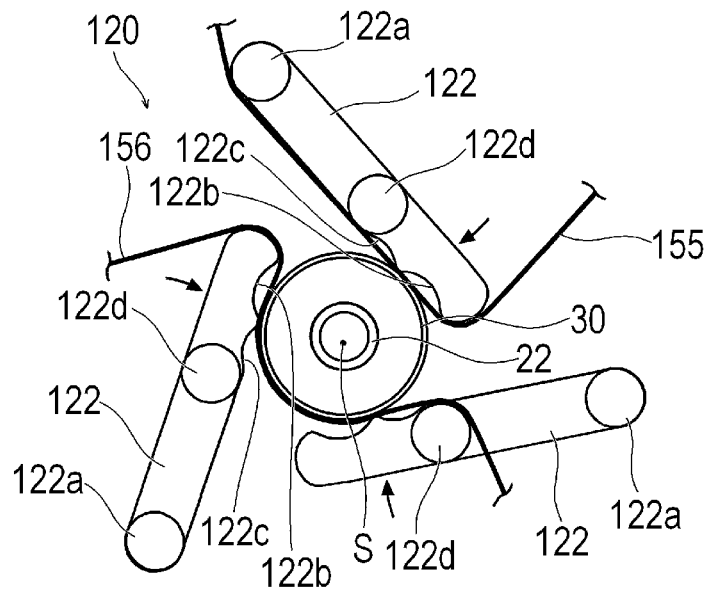
FIG. 9 is a cross-sectional view illustrating a state where a bend of the balloon is corrected by the first blade portions in the pleating section.

Next, when the drive source 125 is operated to rotate the rotation member 124 (see FIG. 4), as illustrated in FIG. 9, the first blade portions 122 move rotationally, vicinities of the first shape pleating portions 122b of the respective first blade portions 122 move closer to one another. Accordingly, the center region among the first blade portions 122 is narrowed to the extent of the outer diameter of the balloon 30, and the first blade portions 122 press the balloon 30 to the center of the center region. Accordingly, the axial center of the balloon 30 is moved closer to the reference position S to correct the bend of the balloon 30. In this case, the balloon 30 in which the pressure-applied state is maintained can be difficult to deform even being pressed by the first blade portions 122. Accordingly, the balloon 30 is effectively pressed by the first blade portions 122 to be positioned to the center of the center region among the first blade portions 122. The balloon 30 in which the pressure-applied state is maintained is pressed by the first blade portions 122 to be guided and positioned to the center region (is not deviated from the center region). The bent portion of the balloon 30 is also pressed by the first blade portions 122 to correct the curve, and is guided and positioned to the center region (is not deviated from the center region). In a case of a state where pressure is not applied to the balloon 30, there is a possibility that the balloon 30 is positioned to a biased position in the center region without being pressed by the first blade portions 122.

Moreover, when the bend of the balloon 30 is corrected, each first blade portion 122 may be vibrated. Accordingly, the balloon 30 is guided to a suitable position by the vibration. The vibration to the first blade portions 122 can be applied, for example, by the drive source 125 (see FIG. 4). Accordingly, the first blade portions 122 vibrate to repeat moving closer to and separating from the balloon 30, and can guide the balloon 30 to the suitable position. The first blade portions 122 may gradually move rotationally toward the reference position S while vibrating, which can effectively guide the balloon 30 to the suitable position. In a case where vibration is applied to the first blade portions 122 by the drive source 125, the vibration of each of the first blade portions 122 can be synchronized. Moreover, the vibration to the first blade portions 122 may be applied by a vibrator, which is different from the drive source 125. The vibration of each of the first blade portions 122 may be synchronized, or does not need to be synchronized. The frequency of the vibration is not specially limited, for example, the frequency of the vibration can be 50 Hz to 1000 Hz.

Next, the pressure applying/reducing device 160 is adjusted to further rotate the rotation member 124 (see FIG. 4) by the drive source 125 while gradually aspirating and discharging the fluid from the balloon 30. Accordingly, as illustrated in FIG. 10, the first blade portions 122 move rotationally. Therefore, the first shape pleating portions 122b of the first blade portions 122 move closer to one another to narrow the center region among the first blade portions 122 to the extent of the outer diameter of the inner tube 22. Accordingly, the balloon 30 inserted into the center region among the first blade portions 122 is pressed against the inner tube 22 by the first shape pleating portion 122b. A portion of the balloon 30 that is not pressed by the first shape pleating portion 122b is pushed out into a gap between a distal end portion of the first blade portion 122 and the second shape pleating portion 122c of the first blade portion 122 adjacent the relevant first blade portion 122 to pleat the wing portion 32 curved in one direction. The first blade portions 122 heat the balloon 30 to approximately 50 degrees Celsius to 60 degrees Celsius. Therefore, the pleated plurality of wing portions 32 can maintain the shape without any change. In this manner, the plurality of wing portions 32 are pleated on the balloon 30. The pressure reduction by the pressure applying/reducing device 160 and the pressure application due to pressing by the first blade portions 122 act on the inside of the balloon 30. The pressure reduction by the pressure applying/reducing device 160 and the pressure application by the first blade portions 122 to be driven by the drive source 125 are adjusted such that the internal pressure in the balloon 30 is maintained to the extent slightly higher than the atmospheric pressure, which can help prevent the balloon 30 from rapidly deflating by the pressure applying/reducing device 160, before the balloon 30 is pressed by the first blade portions 122 to pleat the plurality of wing portions 32 on the balloon 30. Accordingly, the balloon 30 is appropriately pressed by the first blade portions 122 to pleat the plurality of wing portions 32. Note that, when the plurality of wing portions 32 are pleated on the balloon 30, the proximal opening portion 27 may be opened to the atmosphere instead of the aspiration by the pressure applying/reducing device 160. The proximal opening portion 27 can be, for example, rather easily opened by the stopcock 162, which can be a three-way stopcock. After the process of pleating the plurality of wing portions 32 on the balloon 30 has been completed, the state where the pressure in the inside of the balloon 30 is reduced is maintained. For that purpose, the pressure reduction may be continued by the pressure applying/reducing device 160, or the stopcock 162 may be closed.

At the process of pleating the plurality of wing portions 32, a surface of each first blade portion 122 to be contacted the balloon 30 is covered by the first film 155 and the second film 156. Therefore, the balloon 30 does not directly contact the surfaces of the first blade portions 122. After the plurality of wing portions 32 have been pleated on the balloon 30, the first blade portions 122 are moved rotationally so as to return to the original positions. Thereafter, the balloon 30 is pulled out from the pleating section 120.

Next, as illustrated in FIG. 3, the holding stand 142 is moved on the upper surface of the base portion 141 to be separated from the pleating section 120, and to pull out the balloon catheter 10 from the pleating section 120. Next, the support mount 140 is moved by sliding on an upper surface of the base 110 to position the support mount 140 to a position facing the front surface plate 131 of the folding section 130. Thereafter, the holding stand 142 is moved on the upper surface of the base portion 141 to insert the balloon catheter 10 from the insertion hole 131a into the folding section 130. The second blade portions 132 of the folding section 130 can be, for example, already heated to about 50 degrees to 60 degrees. The second blade portions 132, for example, do not need to be heated.

After the balloon 30 with the plurality of wing portions 32 pleated on the balloon 30 has been inserted into the folding section 130, as illustrated in FIG. 6, the drive source 134 is operated to rotate the rotation member 133. Accordingly, as illustrated in FIG. 11, the second blade portions 132 rotate, and the distal end portions 132b of the respective second blade portions 132 move closer to one another. Therefore, the center region among the second blade portions 132 is narrowed. Accordingly, the balloon 30 inserted into the center region among the second blade portions 132 is in a state in which the plurality of wing portions 32 are laid in the circumferential direction by the distal end portions 132*b* of the respective second blade portions 132. The second blade portions 132 are heated in advance before the insertion of the balloon 30, and the balloon 30 is heated by the second blade portions 132, so that the plurality of wing portions 32 laid in the circumferential direction by the second blade portions 132 can maintain the shape without any change. In this case, a surface of each second blade portion 132, which will come into contact with the balloon 30 is covered by the first film 181 and the second film 182. Therefore, the balloon 30 does not contact the surfaces of the second blade portions 132.

After the plurality of wing portions 32 of the balloon 30 have been folded, the second blade portions 132 are moved rotationally so as to return to the original positions. Next, the balloon 30 is pulled out from the folding section 130. Next, the holding of the catheter main body 20 by the holding stand 142 is canceled, and the balloon 30 is inserted into the tubular protective tube 15 (see FIG. 1). This completes the folding of the balloon 30.

As in the foregoing, the folding method of an inflatable balloon according to the present embodiment is a folding method of the balloon 30 disposed on an outer peripheral surface of the inner tube 22 (shaft) of the balloon catheter 10 includes: disposing the balloon 30 to the inner side of the plurality of first blade portions 122 arranged so as to surround the reference position S while maintaining a state where pressure is applied to the inside of the balloon 30; correcting a bend of the balloon 30 by moving the first blade portions 122 toward the reference position S in the state where the pressure is applied to the inside of the balloon 30; pleating a plurality of the wing portions 32 protruding radially outward on the balloon 30 by further moving the first blade portions 122 toward the reference position S to partially press the balloon 30 while gradually discharging the fluid inside the balloon 30; and folding the plurality of wing portions 32 along the inner tube 22. In accordance with an exemplary embodiment, folding the plurality of wing portions 32 along the inner tube 22 indicates that the plurality of wing portions 32 are inclined so as to be tilted toward the inner tube 22. The plurality of wing portions 32, for example, do not need to be entirely folded.

In the folding method of a balloon configured as the above, before the plurality of wing portions 32 are pleated on the balloon 30, the balloon 30 is moved toward the reference position S by the first blade portions 122. In this case, the balloon 30 in the pressure-applied state can be difficult to deform even being pressed by the first blade portions 122. Therefore, in the folding method of a balloon, it is possible to effectively correct the bend of the balloon 30 by moving the balloon 30 toward the reference position S by the first blade portions 122. Accordingly, in the folding method of a balloon, it is possible to uniformly pleat the plurality of wing portions 32 protruding radially outward on the balloon 30. Accordingly, in the folding method of a balloon, it is possible to uniformly fold the plurality of wing portions 32 with respect to the inner tube 22. Accordingly, when the plurality of wing portions 32 are folded in the folding section 130 and the like, the occurrence of a phenomenon of a back fold in which the plurality of wing portions 32 are wound in the opposite direction can be suppressed. Moreover, the balloon 30 are appropriately wound with respect to the inner tube 22, so that the balloon 30 can be smoothly accommodated when being accommodated in the protective tube 15. Therefore, the separation of the drug from the drug-coated layer 40 of the balloon 30 can be suppressed.

Moreover, in this folding method of a balloon, the plurality of wing portions 32 of the balloon 30 are heated at the step of pleating the plurality of wing portions 32 or subsequent steps. Accordingly, it is possible to excellently maintain the shape of the uniformly pleated plurality of wing portions 32 of the balloon 30.

Moreover, in the folding method of a balloon, at the step of correcting the bend of the balloon 30, the first blade portions 122 may be vibrated. Accordingly, it is possible to guide the balloon 30 to a suitable position by the vibration, and to uniformly pleat the plurality of wing portions 32 of the balloon 30.

Moreover, in this folding method of a balloon, at the step of correcting the bend of the balloon 30 and the step of pleating the plurality of wing portions 32, the flexible films 155 and 156 may be interposed between the first blade portions 122 and the balloon 30, and at the step of folding the plurality of wing portions 32, the flexible films 181 and 182 may be interposed between the plurality of second blade portions 132 arranged so as to surround the balloon 30 in order to fold the plurality of wing portions 32 and the balloon 30. Accordingly, when the bend of the balloon 30 is corrected, when the plurality of wing portions 32 are pleated on the balloon 30, and when the plurality of wing portions 32 are folded, it is possible to protect the surface of the balloon 30 by the films, and suppress the separation of the drug from the balloon 30. The forms of the films are not limited the forms described above.

The present disclosure is not limited to the above-described embodiment, but various changes by those skilled in the art can be made within the technical scope of the present disclosure. For example, the balloon catheter 10 according to the above-mentioned embodiment is a rapid exchange type, but may be an over-the-wire type.

Moreover, after the plurality of wing portions 32 have been pleated in the pleating section 120 and before the balloon 30 is folded in the folding section 130, the balloon 30 may be coated with a drug. In this case, the balloon 30 of the balloon catheter 10 to be inserted into the pleating section 120 is not coated with the drug-coated layer 40. Further, after the plurality of wing portions 32 have been pleated in the pleating section 120, a pressure-reduced state in the inside of the balloon 30 is maintained. Accordingly, the pressure in the inside of the balloon 30 may be successively reduced by the pressure applying/reducing device 160, or the stopcock 162 may be closed. Accordingly, the shape of the plurality of wing portions 32 of the balloon 30 can be rather excellently maintained. Next, the balloon 30 is pulled out from the pleating section 120, and the balloon 30 is coated (covered) with the drug-coated layer 40. A method of coating the balloon 30 with the drug-coated layer 40 is not specially limited, and the coating can be performed, for example, by the above-mentioned method of coating the balloon 30 while rotating the balloon 30, dipping, spray, and the like. Thereafter, the balloon 30 with the drug-coated layer 40 being formed is inserted into the folding section 130, and the plurality of wing portions 32 are folded. Accordingly, in a state where the shape of the balloon 30 is held after the plurality of wing portions 32 have been pleated, the surface of the balloon 30 can be appropriately coated with the drug-coated layer 40. Moreover, because the outer surface of the balloon 30 is coated with the drug-coated layer 40 after the plurality of wing portions 32 have been pleated, the outer surface of the balloon 30 is not coated with the drug-coated layer 40 when the plurality of wing portions 32 are pleated. Therefore, when the plurality of wing portions 32 are pleated on the balloon 30, the separation of the drug from the balloon 30 can be suppressed.

Moreover, the above-mentioned folding section 130 does not need to fold the balloon 30. Moreover, the folding method of a balloon may be used for folding the balloon 30 with which no drug-coated layer 40 is coated. Even when the folding method of a balloon according to the present embodiment is used for folding the balloon 30 with which no drug-coated layer 40 is coated, the occurrence of the back fold can be suppressed, and the folded balloon 30 rather easily inflates.

Figure 12:
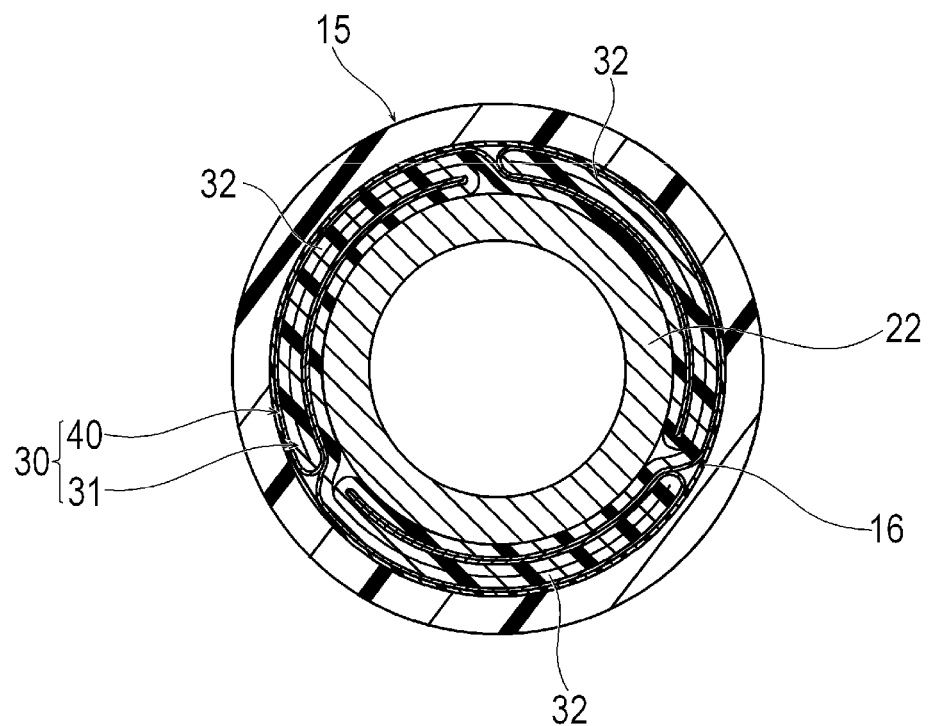
FIG. 12 is a cross-sectional view illustrating a modification example of a balloon catheter.

Moreover, as a modification example illustrated in FIG. 12, the balloon catheter 10 may include a flexible protective film 16 sandwiched between the protective tube 15 and the balloon 30. Accordingly, a drug on the outer surface of the balloon 30 contacts the protective tube 15 via the flexible protective film 16, so that the separation of the drug on the outer surface of the balloon 30 can be suppressed. Moreover, the protective tube 15 is provided to allow the balloon 30 to be inserted into the protective tube 15, and to be taken out from the protective tube 15 in the state where the balloon 30 is kept to be covered with the protective film 16. Therefore, when the balloon 30 is inserted into the protective tube 15 and/or when the balloon 30 is taken out from the protective tube 15, the separation of the drug caused by rubbing of the plurality of wing portions 32 against the protective tube 15 can be suppressed.

Moreover, the pleating section and the folding section may be provided to different devices.

The detailed description above describes embodiments of a method of folding a balloon of a balloon catheter. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A method of folding an inflatable balloon disposed on an outer peripheral surface of a shaft of a balloon catheter, the method comprising:
   horizontally arranging the balloon inside a plurality of first blade portions of a balloon folding device, the plurality of first blade portions being arranged so as to surround a linear reference position while maintaining a state where pressure is being applied to an inside of the balloon, the linear reference position being a center of a center region of the plurality of first blade portions in which the balloon is horizontally arranged;
   rotating the plurality of first blade portions with respect to the balloon in the state where pressure is being applied to the inside of the balloon and moving the plurality of first blade portions toward the linear reference position in the state where the pressure is being applied to the inside of the balloon to correct a bend of the balloon;
   pleating a plurality of wing portions formed from the balloon and protruding radially outward on the balloon by further moving the plurality of first blade portions toward the linear reference position while gradually discharging a fluid from the inside of the balloon to partially press the balloon; and
   folding the plurality of wing portions along the shaft of the balloon catheter.

2. The method of folding the inflatable balloon according to claim 1, further comprising:
   heating the plurality of wing portions on the balloon while pleating the plurality of wing portions protruding radially outward on the balloon.

3. The method of folding the inflatable balloon according to claim 1, the folding further comprising:
   heating the plurality of wing portions on the balloon while folding the plurality of wing portions along the shaft with a plurality of second blade portions of the balloon folding device.

4. The method of folding the inflatable balloon according to claim 1, further comprising:
   vibrating the plurality of first blade portions while correcting the bend of the balloon.

5. The method of folding the inflatable balloon according to claim 1, further comprising:
   regulating an inflow of the fluid to the inside of the balloon after the pleating the of the plurality of wing portions; and
   coating a surface of the balloon with a drug before the folding of the plurality of wing portions along the shaft.

6. The method of folding the inflatable balloon according to claim 1, further comprising:
   interposing a first flexible film between the plurality of first blade portions and the balloon during the moving of the plurality of first blade portions toward the linear reference position in the state where the pressure is being applied to the inside of the balloon and the pleating of the plurality of wing portions.

7. The method of folding the inflatable balloon according to claim 6, further comprising:
   interposing a second flexible film between a plurality of second blade portions of the balloon folding device and the balloon, and surrounding the plurality of folded wing portions of the balloon with the second flexible film.

8. The method of folding the inflatable balloon according to claim 1, wherein the plurality of first blade portions comprises three of the first blade portions, and further comprising:
   arranging the plurality of first blade portions each at an angle of 120 degrees relative to the linear reference positions.

9. The method of folding the inflatable balloon according to claim 1, further comprising:
   disposing the plurality of first blade portions at equal angles in a circumferential direction relative to the balloon.

10. The method of folding the inflatable balloon according to claim 1, wherein an axial center of the balloon is at a position deviated from the linear reference position when the balloon is horizontally arranged inside of the plurality of first blade portions of the balloon folding device.

11. A method of folding an inflatable balloon disposed on an outer peripheral surface of a shaft of a balloon catheter, the method comprising:
   arranging the balloon inside a plurality of first blade portions of a balloon folding device, the plurality of first blade portions being arranged so as to surround a linear reference position while maintaining a state where pressure is being applied to an inside of the balloon and wherein an axial center of the balloon is at a position deviated from the linear reference position, the linear reference position being a center of a center region of the plurality of first blade portions in which the balloon is arranged;
   rotating the plurality of first blade portions with respect to the balloon in the state where pressure is being applied to the inside of the balloon and moving the plurality of first blade portions toward the linear reference position in the state where the pressure is being applied to the inside of the balloon to move the axial center of the balloon to the linear reference position; and pleating a plurality of wing portions formed from the balloon and protruding radially outward on the balloon by further moving the plurality of first blade portions toward the linear reference position while gradually discharging a fluid from the inside of the balloon to partially press the balloon.

12. The method of folding the inflatable balloon according to claim 11, further comprising:

folding the plurality of wing portions along the shaft of the balloon catheter.

13. The method of folding the inflatable balloon according to claim 12, further comprising:

regulating an inflow of the fluid to the inside of the balloon after the pleating the of the plurality of wing portions; and coating a surface of the balloon with a drug before the folding of the plurality of wing portions along the shaft.

14. The method of folding the inflatable balloon according to claim 11, the folding further comprising:

heating the plurality of wing portions on the balloon while folding the plurality of wing portions along the shaft with a plurality of second blade portions of the balloon folding device.

15. The method of folding the inflatable balloon according to claim 11, further comprising:

vibrating the plurality of first blade portions while correcting the deviated position of the axial center of the balloon.

16. The method of folding the inflatable balloon according to claim 11, further comprising:

interposing a first flexible film between the plurality of first blade portions and the balloon during the moving of the plurality of first blade portions toward the linear reference position in the state where the pressure is being applied to the inside of the balloon and the pleating of the plurality of wing portions.

* * * * *